United States Patent

Bost et al.

[11] 4,113,779
[45] Sep. 12, 1978

[54] PREPARATION OF KETONES

[75] Inventors: Pierre-Etienne Bost, Paris; Guy Lartigau, Rhone, both of France

[73] Assignee: Rhone-Poulenc S.A., Paris, France

[21] Appl. No.: 473,267

[22] Filed: May 24, 1974

[30] Foreign Application Priority Data

May 28, 1973 [FR] France .................. 73.19288

[51] Int. Cl.² ........................................... C07C 45/00
[52] U.S. Cl. .................................................... 260/592
[58] Field of Search .................. 260/592, 593 A, 621

[56] References Cited

U.S. PATENT DOCUMENTS

| | | | |
|---|---|---|---|
| 2,557,968 | 6/1951 | Hulse et al. | 260/592 |
| 3,531,519 | 9/1970 | Parkin et al. | 260/592 |

OTHER PUBLICATIONS

Seiichiro et al., Chem. Abst., vol. 78, 151982h, (1973).

Primary Examiner—James O. Thomas, Jr.
Assistant Examiner—James H. Reamer
Attorney, Agent, or Firm—Cushman, Darby & Cushman

[57] ABSTRACT

A process is provided for the preparation of aryl ketones by catalytic decomposition of tertiary hydroperoxides, in particular for the preparation of acetophenone from cumene hydroperoxide, said process comprising effecting the catalytic decomposition of a tertiary hydroperoxide of the formula:

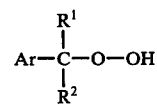

in which Ar represents a monovalent aromatic radical, the free valency of which is carried by a carbon atom belonging to an aromatic ring, and $R^1$ and $R^2$, which may be identical or different, each represents a monovalent aliphatic radical or $R^1$ and $R^2$ together form a divalent aliphatic radical, in a reaction medium comprising water, an inorganic or organic derivative of copper and a phenol, and at a temperature of from 50° C to 150° C.

18 Claims, No Drawings

PREPARATION OF KETONES

The present invention relates to an improved process for the catalytic decomposition of aryldialkylmethyl hydroperoxides to yield aromatic ketones, and more particularly for the decomposition of cumene hydroperoxide (CHPO) to yield acetophenone.

More specifically, the present invention provides a process for the preparation of an aryl ketone which comprises effecting the catalytic decomposition of a tertiary hydroperoxide of the formula:

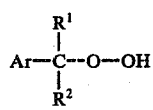

in which Ar represents a monovalent aromatic radical, the free valency of which is carried by a carbon atom belonging to an aromatic ring, and $R^1$ and $R^2$, which may be identical or different, each represents an aliphatic radical or $R^1$ and $R^2$ together form a divalent aliphatic radical, in a reaction medium comprising water, an inorganic or organic derivative of copper and a phenol, the reaction temperature being above 50° C and below 150° C.

The aromatic radical Ar can contain substituents as long as the carbon atom carrying the free valency of Ar is part of an aromatic ring. Ar can, for example, represent a phenyl radical or a naphthyl radical, optionally substituted by, for example, one or more halogen atoms or nitro, cyano, alkyl or alkoxy radicals, the latter radicals preferably having 1 to 4 carbon atoms. The number of substituents on an aromatic ring is preferably not more than 3.

$R^1$ and $R^2$ preferably each represents an alkyl radical having at most 4 carbon atoms; if $R^1$ and $R^2$ together form a divalent aliphatic radical, it is preferably an alkylene radical with 3 to 11 carbon atoms.

Specific examples of hydroperoxides which may be used are cumene hydroperoxide, ortho- and para-nitrocumene hydroperoxides, α,α-dimethyl-para-methylbenzyl hydroperoxide, α,α-dimethyl-para-isopropylbenzyl hydroperoxide, α-ethyl-α-methylbenzyl hydroperoxide, α,α-dimethylnaphthylmethyl hydroperoxide and 1-phenyl-cyclohexyl hydroperoxide. The preferred hydroperoxide is cumene hydroperoxide.

It is also possible to prepare diketones from dihydroperoxides, such as α,α,α',α'-tetramethyl-para-xylylene hydroperoxides, in which the radical Ar contains a substituent of the formula:

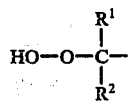

wherein $R^1$ and $R^2$ are as hereinbefore defined.

When $R^1$ and $R^2$ each represents a monovalent aliphatic radical, the product of the process of the invention consists predominantly of aromatic ketones of the formula Ar—CO—R in which R represents $R^1$ or $R^2$ (aliphatic alcohols are obtained as by products).

When $R^1$ and $R^2$, taken together, form a divalent radical R', the principal product of the process of the invention is an aromatic ketone with an alcohol group, said ketone having the formula Ar—CO—R'—OH.

The relative amounts of water and hydroperoxide in the reaction medium are preferably such that the ratio by weight of hydroperoxide to water is from $10^{-4}$ to 10, especially from 0.01 to 0.3.

The organic or inorganic derivative of copper is preferably soluble in the aqueous phase (i.e. the single phase of the reaction mixture if the latter is homogeneous, or, if the latter is heterogeneous, the phase which has the maximum content of water). The preferred copper derivatives are organic or inorganic cupric or cuprous salts. The preferred salts are those of strong inorganic acids, especially nitrates, sulphates, perchlorates and halides, or carboxylates, especially acetates, propionates or butyrates. Copper compounds which yield such derivatives under the reaction conditions can also be used.

The amount of copper derivative employed is preferably such that the ratio of the number of mols of hydroperoxide in the reaction mixture to the number of gram atoms of copper in the copper derivative is from 5 to $10^4$, especially from 10 to $10^3$.

The phenol used in the process of the invention acts as a co-catalyst. It can be a mono- or a poly-phenol (i.e. a polyhydroxylic aromatic compound). The phenol may, for example, have the formula ArOH, in which Ar is as hereinbefore defined, or HO—Ar'—OH where Ar' is the aromatic part of a dihydroperoxide; such phenols can be regarded as being derived from the hydroperoxides defined above by replacement of the hydroperoxide group

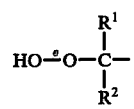

by a hydroxyl group.

The preferred mono-phenols are phenol, ortho- meta- and para-cresols, dimethyl-phenols, isopropyl-phenols and α- and β-naphthols; suitable poly-phenols are hydroquinone, resorcinol, pyrocatechol, hydroanthraquinone, trihydroxybenzenes, bis-(para-hydroxyphenyl)-methane and 2,2-bis-(para-hydroxyphenol)-propane.

The amount of phenol used is preferably such that: the ratio of the number of mols of phenol to the number of gram atoms of copper in the copper derivative is from 0.01 to 2, especially from 0.1 to 1 and the molar ratio of phenol to hydroperoxide is greater than $10^{-3}$, preferably greater than $10^{-2}$.

The phenol used as co-catalyst can be introduced as such into the reaction medium or can be formed in situ by decomposition of a suitable amount of the tertiary hydroperoxide in the presence of an acid catalyst of the type used in the decomposition of tertiary alkylaromatic hydroperoxides to yield phenols. The acid catalyst may be introduced, at the same time as the copper derivative; suitable such acid catalysts are protonic acids, particularly highly dissociated protonic acids, for example, sulphuric acid, nitric acid, perchloric acid, trifluoroacetic acid and sulphonic acids, such as methanesulphonic and benzenesulphonic acid.

The amount of acid catalyst needed to form the requisite amount of phenol is calculated such that the ratio (number of mols of phenol/number of gram atoms of copper) and the molar ratio of phenol to hydroperoxide lie within the limits defined above. This amount varies depending on the strength of the acid; in practice the pH of the aqueous phase is less than 4, preferably from 2 to 3.5.

Some of the copper derivatives which are suitable for use in the process of the invention can, under the reaction conditions, bring about partial acid splitting of the hydroperoxide to yield a phenol, liberating a strong acid as a result of hydrolysis; in this case, it is not necessary to introduce a phenol or an acid catalyst. Cupric perchlorate is an example of a copper derivative of this type.

The reaction mixtue can contain other substances such as adjuvants or solvents (other than water). In the case of the decomposition of CHPO to yield acetophenone, dimethylphenylcarbinol (2-phenyl-2-propanol) or α-methylstyrene is advantageously used as an adjuvant; these adjuvants are preferably used in an amount of from 0.5 to 4 times (in mols) the amount of CHPO.

If a solvent is used, it is preferably a solvent for the hydroperoxide, which is insoluble in water and inert, under the working conditions, with respect to the various products present in the medium. Examples of suitable solvents are cycloaliphatic or aromatic hydrocarbons, especially cycloalkanes, benzene, cumene or ethers.

The reaction temperature is preferably from 80° C to 120° C; in a preferred embodiment of the invention the reaction is carried out at the reflux temperature of the reaction mixture in order to avoid working under pressure.

The process of the invention makes it possible to obtain ketones in good yields under relatively mild conditions. Another advantage is the fact that aliphatic alcohols are generally obtained as by-products.

The following Examples illustrate the invention.

EXAMPLES 1 TO 6

A series of experiments involving the decomposition of cumene hydroperoxide (CHPO) to yield acetophenone are carried out in accordance with the following general procedure:

The catalyst, water, the phenol or an acid catalyst for the formation of the phenol (except when the above-mentioned catalyst is copper perchlorate), are introduced successively into a glass flask equipped with a stirrer and a reflux condenser.

The mixture is then heated to the desired temperature (Θ) and CHPO is run into the mixture. The mixture is refluxed for a period of time t. At the end of the reaction, the mixture is cooled, an extraction with benzene is effected and the amounts of products formed are measured.

Table I gives the working conditions and the results obtained for the various Examples. Example 4bis, in which no phenol, acid catalyst or copper perchlorate is used, is included by way of comparison.

TABLE I

| Ex. No. | Catalyst Nature | Catalyst Amount is m. mols | Water in cm³ | Phenol or acid catalyst Nature | Phenol or acid catalyst Amount in m. mols | CHPO in mols | θ(°C) decomposition temperature | t duration, in minutes, of the reaction | pH of the aqueous phase | Number of phases | Degree of conversion, in % | Yield of acetophenone, in % |
|---|---|---|---|---|---|---|---|---|---|---|---|---|
| 1 | Cu(ClO₄)₂ . 6 H₂O | 5 | 100 | none | 0 | 0.1 | 98 | 95 | 3.5 | 2 | 100 | 88.7 |
| 2 | Cu(NO₃)₂ . 3 H₂O | 5 | 100 | HNO₃ | 1 | 0.1 | 98 | 30 | 2.1 | 2 | 100 | 88.5 |
| 3 | Cu(NO₃)₂ . 3 H₂O | 5 | 100 | phenol | 2 | 0.1 | 96 | 100 | — | 2 | 100 | 97.5 |
| 4 | Cu(OCOCH₃)₂ | 2.5 | 50 | " | 1 | 0.05 | 100 | 180 | — | 2 | 99 | 71.5 |
| 4bis (comparison) | Cu(OCOCH₃)₂ | 2.5 | 50 | none | 0 | 0.05 | 100 | 180 | — | 2 | 99 | 49.7 |
| 5 | Cu(NO₃)₂ . 3 H₂O | 2.5 | 50 | hydroquinone | 1 | 0.05 | 98 | 60 | — | 2 | 99 | 88.7 |
| 6 | Cu(NO₃)₂ . 3 H₂O | 2.5 | 50 | pyrocatechol | 5 | 0.05 | 99 | 60 | — | 2 | 100 | 79.4 |

We claim:

1. A process for the preparation of an aryl ketone which comprises effecting the catalytic decomposition of a tertiary hydroperoxide of the formula:

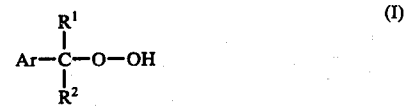
(I)

in which Ar represents a monovalent aromatic radical, the free valency of which is carried by a carbon atom belonging to an aromatic ring, and R¹ and R², which may be identical or different, each represents a monovalent aliphatic radical or R¹ and R² together form a divalent aliphatic radical, in an acidic reaction medium comprising water, a catalytic amount of a water-soluble inorganic or organic cupric salt such that the ratio of the number of mols of hydroperoxide to the number of gram-atoms of copper in the cupric salt is from 5 to 10⁴ and a phenol of the formula Ar-OH in which Ar is as defined above, the ratio of the number of mols of phenol to the number of grams of copper in the copper salt being from 0.01 to 2, and at a temperature of from 50° C. to 150° C.

2. A process according to claim 1 in which Ar represents a phenyl or naphthyl radical optionally substituted by one or more halogen atoms or nitro, cyano or $C_{1-4}$ alkyl or alkoxy radicals.

3. A process according to claim 1, in which R¹ and R² each independently represents an alkyl radical with 1 to 4 carbon atoms.

4. A process according to claim 3, in which the hydroperoxide is ortho- or para-nitrocumene hydroperoxide, α,α-dimethyl-para-methylbenzyl hydroperoxide, α,α-dimethyl-para-isopropylbenzyl hydroperoxide, α-ethyl-α-methylbenzyl hydroperoxide or α,α-dimethylnaphthylmethyl hydroperoxide.

5. A process according to claim 1, in which the hydroperoxide is cumene hydroperoxide.

6. A process according to claim 1, in which $R^1$ and $R^2$ together form an alkylene radical with 3 to 11 carbon atoms.

7. A process according to claim 6, in which the hydroperoxide is 1-phenyl-cyclohexyl hydroperoxide.

8. A process according to claim 1, in which the hydroperoxide is a dihydroperoxide in which the radical Ar contains a substituent of the formula:

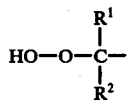

wherein $R^1$ and $R^2$ are as defined in claim 1.

9. A process according to claim 8, wherein the dihydroperoxide is α,α,α',α'-tetramethyl-para-xylylene hydroperoxide.

10. A process according to claim 1, wherein the ratio by weight of hydroperoxide to water in the reaction medium is from $10^{-4}$ to 10.

11. A process according to claim 10, wherein the ratio by weight of hydroperoxide to water is from 0.01 to 0.3.

12. A process according to claim 1, wherein the copper salt is cupric perchlorate.

13. A process according to claim 1, wherein the ratio of the number of mols of hydroperoxide in the reaction mixture to the number of gram atoms of copper in the copper salt is from 10 to $10^3$.

14. A process according to claim 17, wherein the ratio of the number of mols of phenol to the number of gram atoms of copper in the copper salt is from 0.1 to 1 and the molar ratio of phenol to hydroperoxide is greater than $10^{-2}$.

15. A process according to claim 1, wherein the phenol is formed in the reaction medium by partial decomposition of the hydroperoxide of the formula (I) by a protonic acid selected from sulphuric acid, nitric acid, perchloric acid, trifluoroacetic acid, methanesulphonic acid and benzenesulphonic acid, said acid either being introduced at the same time as the inorganic or organic cupric salt, or being formed in situ in the reaction medium, said acid being present in an amount such that the pH is less than 4.

16. A process according to claim 1, wherein the reaction mixture also contains at least one adjuvant or solvent selected from cycloaliphatic and aromatic hydrocarbons.

17. A process according to claim 1, wherein the molar ratio of phenol to hydroperoxide is greater than $10^{-3}$.

18. A process according to claim 15, wherein the aqueous phase of the reaction mixture has a pH of from 2 to 3.5.